(12) United States Patent
Zhou et al.

(10) Patent No.: US 9,677,080 B2
(45) Date of Patent: Jun. 13, 2017

(54) METHOD OF ELIMINATING DEPENDENCE OF METHANOL INDUCED PROMOTER ON SINGLE METHANOL CARBON SOURCE

(71) Applicant: EAST CHINA UNIVERSITY OF SCIENCE AND TECHNOLOGY, Shanghai (CN)

(72) Inventors: Xiangshan Zhou, Shanghai (CN); Yuanxing Zhang, Shanghai (CN); Jinjia Wang, Shanghai (CN); Xiaolong Wang, Shanghai (CN); Peng Bai, Shanghai (CN); Ping Zhang, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days.

(21) Appl. No.: 14/413,930

(22) PCT Filed: Nov. 15, 2012

(86) PCT No.: PCT/CN2012/084642
§ 371 (c)(1),
(2) Date: Jan. 9, 2015

(87) PCT Pub. No.: WO2014/008729
PCT Pub. Date: Jan. 16, 2014

(65) Prior Publication Data
US 2015/0299716 A1 Oct. 22, 2015

(30) Foreign Application Priority Data
Jul. 12, 2012 (CN) .......................... 2012 1 0196862

(51) Int. Cl.
*C12P 21/06* (2006.01)
*C12N 1/00* (2006.01)
*C12N 15/81* (2006.01)
*C07K 14/39* (2006.01)
*C12N 1/32* (2006.01)
*C12P 21/00* (2006.01)

(52) U.S. Cl.
CPC ............ *C12N 15/815* (2013.01); *C07K 14/39* (2013.01); *C12N 1/32* (2013.01); *C12P 21/00* (2013.01)

(58) Field of Classification Search
None
See application file for complete search history.

(56) References Cited

U.S. PATENT DOCUMENTS

| 8,143,023 | B2 | 3/2012 | Takagi et al. |
| 8,236,528 | B2 | 8/2012 | Takagi et al. |
| 2009/0311749 | A1 | 12/2009 | Takagi et al. |
| 2012/0142053 | A1 | 6/2012 | Tsutsumi et al. |

FOREIGN PATENT DOCUMENTS

| CN | 101589146 A | 11/2009 |
| CN | 101857845 A | 10/2010 |
| CN | 102757976 A | 10/2012 |

OTHER PUBLICATIONS

Mille et. al. Inactivation of CaMIT1 Inhibits Candida albicans Phospholipomannan Beta-Mannosylation, Reduces Virulence, and Alters Cell Wall Protein Beta-Mannosylation. J. Biol. Chem. 279(46): 47952-47960, 2004.*
Inan et al. Non-repressing carbon sources for alcohol oxidase (AOX1) promoter of Pichia pastoris. J Biosci Bioeng. 2001;92(6):585-9.*
pGEM-t vector map. www.promega.com. 2015.*
Stasyk 2007. The role of Hanseula polymorpha MIG1 homologues in catabolite repression and pexophagy. Sep. 10, 2007. Yeast Research. vol. 7, Issue 7, pp. 1103-1113.*
Stasyk 2008. Identification of Hexose Transporter-Like Sensor HXS1 and Functional Hexose Transporter HXT1 in the Methylotrophic Yeast Hansenula polymorpha. Apr. 2008. Eukaryotic Cell. vol. 7, No. 4, pp. 735-746.*
Cai, Mengnan, "Glycerol-limitation-induced production of recombinant proteins in Hansenula polymorpha", Master's Degree Thesis of Institute of Microbiology and Biochemistry, National Taiwan University, May 11, 2010 (Nov. 5, 2010).
De, S.K., "Pichia pastoris GS115 hypothetical protein (PAS_chr3_0836) mRNA, complete cds", GenBank accession No. XM_002493021, Jul. 22, 2009 (Jul. 22, 2009).
International Search Report for PCT/CN2012/084642 mailed Apr. 18, 2013; ISA/CN.
Lin-Cereghino, G.P. et al., "Mxr1p, a key regulator of the methanol Utilization pathway and peroxisomal genes in Pichia pastoris", Molecular and Cellular Biology, vol. 26, No. 5, pp. 883-897, Feb. 2006.
Stasyk, O., Nazarko, T., and Sibirny, A. Methods of Plate Pexophagy Monitoring and Positive Selection for ATG Gene Cloning in Yeasts. Methods in Enzymology, vol. 451. ISSN 0076-6879, DOI: 10.1016/S0076-6879(08)03216-3. (2008) pp. 229-239.
Verduyn, C., van Dijken, J., and Scheffers, W.A., Colorimetric alcohol assays with alcohol oxidase. Journal of Microbiological Methods 2. Elsevier. (1984) pp. 15-25.
Xuan, Y., Zhou, X., Zhang, W. Zhang, X., Song, Z. and Zhang., Y. An upstream activiation sequence controls the expression of AOX1 gene in Pichia pastoris. FEMS Yeast Res 9 (2009) pp. 1271-1282.
Ying, Guoxin, "Screening of the Differentially Expressed Genes and Cystatin C Expression in the Deafferented Hippocampus", China Doctoral Dissertations Full-Text Database (Basic Sciences), ISSN 1671-6779, 2003, No. 2, Jul. 20, 2003 (Jul. 20, 2003), p. 32.

* cited by examiner

*Primary Examiner* — Channing S Mahatan
(74) *Attorney, Agent, or Firm* — Harness, Dickey & Pierce, P.L.C.

(57) ABSTRACT

Provided is a method of eliminating the dependence of methanol induced promoter on a single methanol carbon source for expressing foreign polypeptide. The method comprises activating the expression of the promoter requiring methanol induction by increasing the expression quantity of Mit1 polypeptide in cells of methylotrophic yeast, so that the promoter originally depending on methanol induction no longer depends on single methanol and can also express foreign polypeptide.

11 Claims, 4 Drawing Sheets

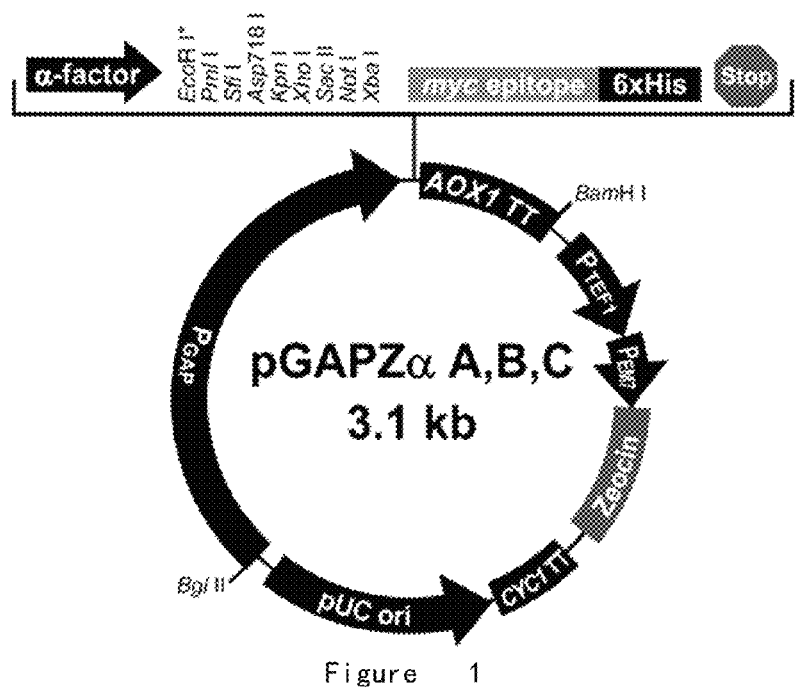
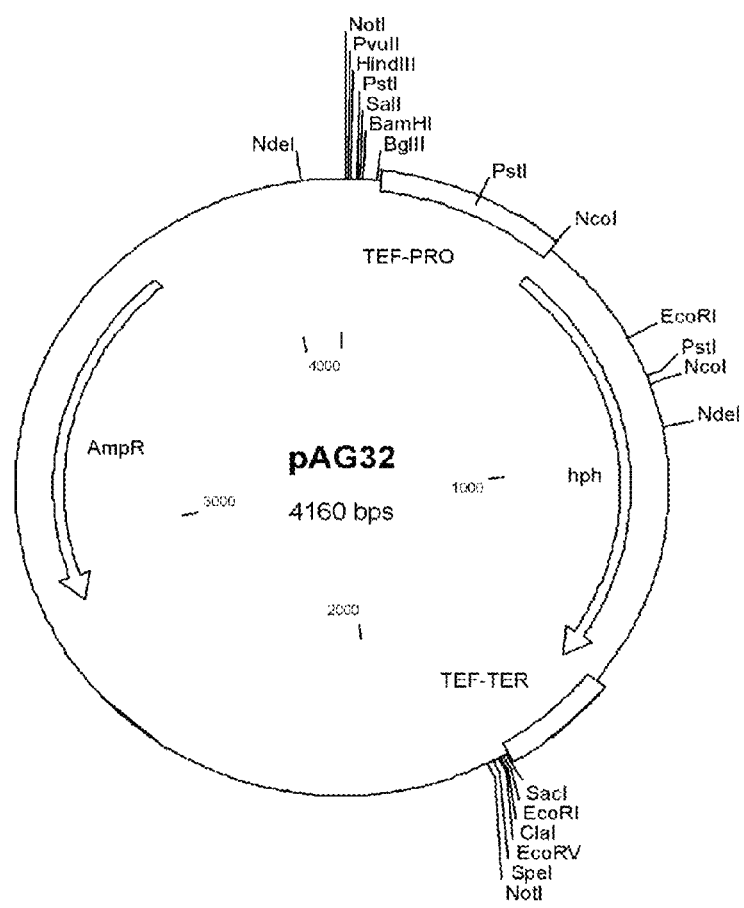
Figure 1
Figure 2

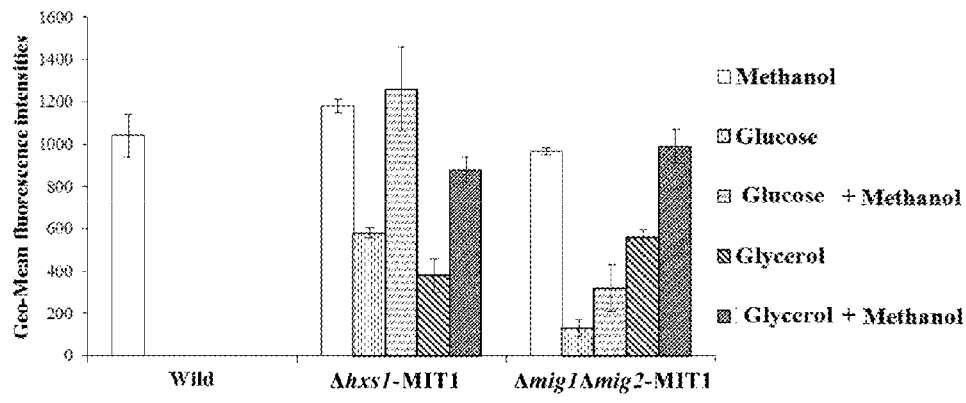
Figure 8
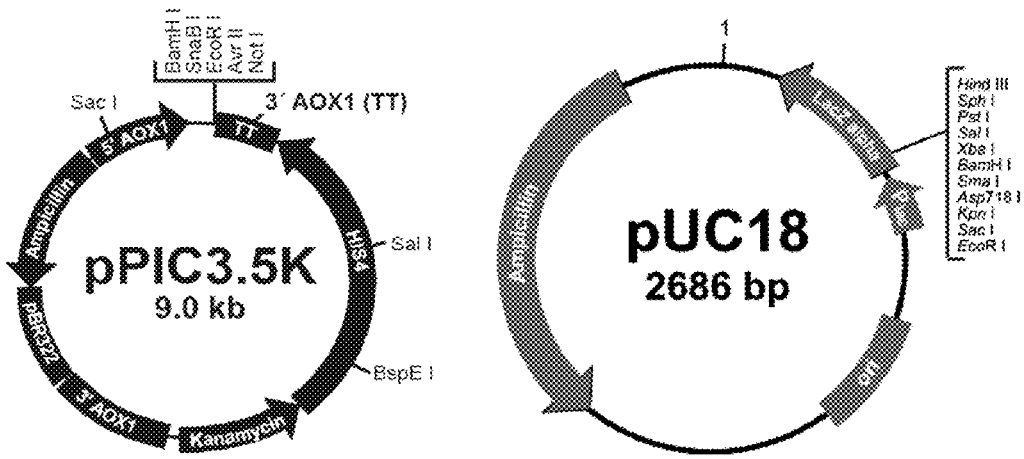
Figure 9
Figure 10
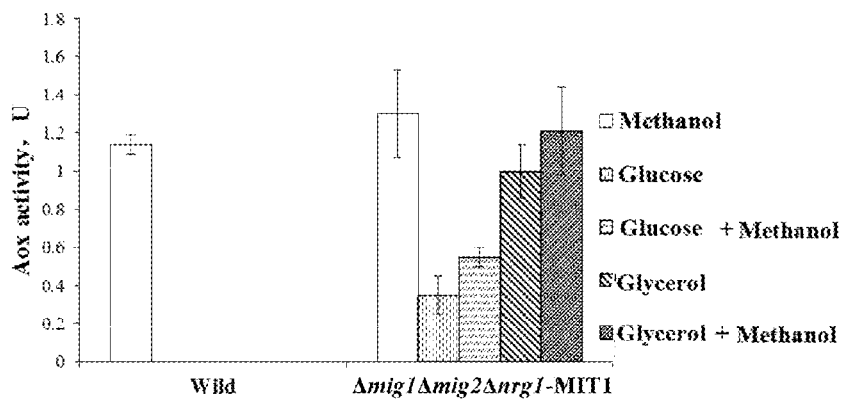
Figure 11

SEQUENCE LISTING

<160> NUMBER OF SEQ ID NOS: 22

<210> SEQ ID NO 1
<211> LENGTH: 2667

```
<212> TYPE: DNA
<213> ORGANISM: Pichia pastoris

<400> SEQUENCE: 1
atgagtaccg cagccccaat caaggaagaa agccaatttg cccatttgac cctaatgaac      60
aaggatatac cttcgaacgc aaaacaggca aagtcgaaag tttcagcggc ccctgctaag     120
acgggctcca aatctgctgg tggatctggc aacaacaacg ctgcacctgt gaaaaaaaga     180
gtccgcacgg gctgtttgac ctgccgaaag aagcacaaga aatgtgacga aacagaaac      240
ccaaaatgtg acttttgcac tttgaaaggc ttggaatgtg tctggccaga gaacaataag     300
aagaatatct tcgttaacaa ctccatgaag gatttcttag caagaaaaac ggtggatgga     360
gctgatagtc tcaatttggc cgtgaatctg caacaacagc agagttcaaa cacaattgcc     420
aatcaatcgc tttcctcaat tggattggaa agttttggtt acggctctgg tatcaaaaac     480
gagtttaact tccaagactt gataggttca aactctggca gttcagatcc gacattttca     540
gtagacgctg acgaggccca aaaactcgac atttccaaca agaacagtcg taagagacag     600
aaactaggtt tgctgccggt cagcaatgca acttcccatt gaacggtttt caatggaatg     660
tccaatggaa agtcacactc tttctcttca ccgtctggga ctaatgacga tgaactaagt     720
ggcttgatgt tcaactcacc aagcttcaac ccctcacag ttaacgattc taccaacaac      780
agcaaccaca ataggtttt gtctccgatg tcatgcttat tttctacagt tcaagaagca     840
tctcaaaaaa agcatggaaa ttccagtaga cacttttcat acccatctgg gccggaggac     900
ctttggttca atgagttcca aaaacaggcc ctcacagcca atggagaaaa tgctgtccaa     960
cagggagatg atgcttctaa gaacaacaca gccattccta aggaccagtc ttcgaactca    1020
tcgattttca gttcacgttc tagtgcagct tctagcaact caggagacga tattggaagg    1080
atgggcccat tctccaaagg accagagatt gagttcaact acgattcttt tttggaatcg    1140
ttgaaggcag agtcaccctc ttcttcaaag tacaatctgc cggaaacttt gaaagagtac    1200
atgacccttg gttcgtctca tctgaatagt caacactccg acactttggc aaatggcact    1260
aacggtaact attctagcac cgttttccaac aacttgagct taagtttgaa ctccttctct    1320
ttctctgaca gttctcatt gagtccacca acaatcactg acgccgaaaa gttttcattg    1380
atgagaaact tcattgacaa catctcgcca tggtttgaca cttttgacaa taccaaacag    1440
tttgaaacaa aaattccagt tctggccaaa aaatgttctt cattgtacta tgccattctg    1500
gctatatctt ctcgtcaaag agaaaggata aagaaagagc acaatgaaaa aacattgcaa    1560
tgctaccaat actcactaca acagctcatc cctactgttc aaagctcaaa taatattgag    1620
tacattatca catgtattct cctgagtgtg ttccacatca tgtctagtga accttcaacc    1680
cagagggaca tcattgtgtc attggcaaaa tacattcaag catgcaacat aaacggattt    1740
acatctaatg acaaactgga aaagagtatt ttctggaact atgtcaattt ggatttggct    1800
acttgtgcaa tcggtgaaga gtcaatggtc attccttta gctactgggt taaagagaca    1860
actgactaca agaccattca agatgtgaag ccattttttca ccaagaagac tagcacgaca    1920
actgacgatg acttggacga tatgtatgcc atctacatgc tgtacattag tggtagaatc    1980
attaacctgt tgaactgcag agatgcgaag ctcaattttg agcccaagtg ggagttttg    2040
tggaatgaac tcaatgaatg ggaattgaac aaacccttga cctttcaaag tattgttcag    2100
ttcaaggcca atgacgaatc gcagggcgga tcaacttttc caactgttct attctccaac    2160
tctcgaagct gttacagtaa ccagctgtat catatgagct acatcatctt agtgcagaat    2220
```

```
aaaccacgat tatacaaaat cccctttact acagtttctg cttcaatgtc atctccatcg    2280
gacaacaaag ctgggatgtc tgcttccagc acacctgctt cagaccacca cgcttctggt    2340
gatcatttgt ctccaagaag tgtagagccc tctctttcga aacgttgag ccctccgcct     2400 aatgcaaacg gtgcaggtaa caagttccgc tctacgctct ggcatgccaa gcagatctgt    2460
gggatttcta tcaacaacaa ccacaacagc aatctagcag ccaaagtgaa ctcattgcaa    2520
ccattgtggc acgctggaaa gctaattagt tccaagtctg aacatacaca gttgctgaaa    2580
ctgttgaaca accttgagtg tgcaacaggc tggcctatga actggaaggg caaggagtta    2640
attgactact ggaatgttga agaatag                                         2667
```

<210> SEQ ID NO 2
<211> LENGTH: 888
<212> TYPE: PRT
<213> ORGANISM: Pichia pastoris

<400> SEQUENCE: 2

```
Met Ser Thr Ala Ala Pro Ile Lys Glu Glu Ser Gln Phe Ala His Leu
 1               5                  10                  15

Thr Leu Met Asn Lys Asp Ile Pro Ser Asn Ala Lys Gln Ala Lys Ser
            20                  25                  30

Lys Val Ser Ala Ala Pro Ala Lys Thr Gly Ser Lys Ser Ala Gly Gly
        35                  40                  45

Ser Gly Asn Asn Asn Ala Ala Pro Val Lys Lys Arg Val Arg Thr Gly
    50                  55                  60

Cys Leu Thr Cys Arg Lys Lys His Lys Lys Cys Asp Glu Asn Arg Asn
65                  70                  75                  80

Pro Lys Cys Asp Phe Cys Thr Leu Lys Gly Leu Glu Cys Val Trp Pro
                85                  90                  95

Glu Asn Asn Lys Lys Asn Ile Phe Val Asn Asn Ser Met Lys Asp Phe
            100                 105                 110

Leu Gly Lys Lys Thr Val Asp Gly Ala Asp Ser Leu Asn Leu Ala Val
        115                 120                 125

Asn Leu Gln Gln Gln Gln Ser Ser Asn Thr Ile Ala Asn Gln Ser Leu
    130                 135                 140

Ser Ser Ile Gly Leu Glu Ser Phe Gly Tyr Gly Ser Gly Ile Lys Asn
145                 150                 155                 160

Glu Phe Asn Phe Gln Asp Leu Ile Gly Ser Asn Ser Gly Ser Ser Asp
                165                 170                 175

Pro Thr Phe Ser Val Asp Ala Asp Glu Ala Gln Lys Leu Asp Ile Ser
            180                 185                 190

Asn Lys Asn Ser Arg Lys Arg Gln Lys Leu Gly Leu Leu Pro Val Ser
        195                 200                 205

Asn Ala Thr Ser His Leu Asn Gly Phe Asn Gly Met Ser Asn Gly Lys
    210                 215                 220

Ser His Ser Phe Ser Ser Pro Ser Gly Thr Asn Asp Asp Glu Leu Ser
225                 230                 235                 240

Gly Leu Met Phe Asn Ser Pro Ser Phe Asn Pro Leu Thr Val Asn Asp
                245                 250                 255

Ser Thr Asn Asn Ser Asn His Asn Ile Gly Leu Ser Pro Met Ser Cys
            260                 265                 270

Leu Phe Ser Thr Val Gln Glu Ala Ser Gln Lys Lys His Gly Asn Ser
        275                 280                 285

Ser Arg His Phe Ser Tyr Pro Ser Gly Pro Glu Asp Leu Trp Phe Asn
```

```
            290                 295                 300
Glu Phe Gln Lys Gln Ala Leu Thr Ala Asn Gly Glu Asn Ala Val Gln
305                 310                 315                 320

Gln Gly Asp Asp Ala Ser Lys Asn Asn Thr Ala Ile Pro Lys Asp Gln
                325                 330                 335

Ser Ser Asn Ser Ser Ile Phe Ser Ser Arg Ser Ser Ala Ala Ser Ser
            340                 345                 350

Asn Ser Gly Asp Asp Ile Gly Arg Met Gly Pro Phe Ser Lys Gly Pro
                355                 360                 365

Glu Ile Glu Phe Asn Tyr Asp Ser Phe Leu Glu Ser Leu Lys Ala Glu
            370                 375                 380

Ser Pro Ser Ser Ser Lys Tyr Asn Leu Pro Glu Thr Leu Lys Glu Tyr
385                 390                 395                 400

Met Thr Leu Ser Ser Ser His Leu Asn Ser Gln His Ser Asp Thr Leu
                405                 410                 415

Ala Asn Gly Thr Asn Gly Asn Tyr Ser Ser Thr Val Ser Asn Asn Leu
            420                 425                 430

Ser Leu Ser Leu Asn Ser Phe Ser Phe Ser Asp Lys Phe Ser Leu Ser
            435                 440                 445

Pro Pro Thr Ile Thr Asp Ala Glu Lys Phe Ser Leu Met Arg Asn Phe
450                 455                 460

Ile Asp Asn Ile Ser Pro Trp Phe Asp Thr Phe Asp Asn Thr Lys Gln
465                 470                 475                 480

Phe Gly Thr Lys Ile Pro Val Leu Ala Lys Lys Cys Ser Ser Leu Tyr
                485                 490                 495

Tyr Ala Ile Leu Ala Ile Ser Ser Arg Gln Arg Glu Arg Ile Lys Lys
            500                 505                 510

Glu His Asn Glu Lys Thr Leu Gln Cys Tyr Gln Tyr Ser Leu Gln Gln
            515                 520                 525

Leu Ile Pro Thr Val Gln Ser Ser Asn Asn Ile Glu Tyr Ile Ile Thr
            530                 535                 540

Cys Ile Leu Leu Ser Val Phe His Ile Met Ser Ser Glu Pro Ser Thr
545                 550                 555                 560

Gln Arg Asp Ile Ile Val Ser Leu Ala Lys Tyr Ile Gln Ala Cys Asn
                565                 570                 575

Ile Asn Gly Phe Thr Ser Asn Asp Lys Leu Glu Lys Ser Ile Phe Trp
                580                 585                 590

Asn Tyr Val Asn Leu Asp Leu Ala Thr Cys Ala Ile Gly Glu Glu Ser
            595                 600                 605

Met Val Ile Pro Phe Ser Tyr Trp Val Lys Glu Thr Thr Asp Tyr Lys
            610                 615                 620

Thr Ile Gln Asp Val Lys Pro Phe Phe Thr Lys Lys Ser Thr Thr
625                 630                 635                 640

Thr Asp Asp Asp Leu Asp Asp Met Tyr Ala Ile Tyr Met Leu Tyr Ile
                645                 650                 655

Ser Gly Arg Ile Ile Asn Leu Leu Asn Cys Arg Asp Ala Lys Leu Asn
            660                 665                 670

Phe Glu Pro Lys Trp Glu Phe Leu Trp Asn Gly Leu Asn Glu Trp Glu
            675                 680                 685

Leu Asn Lys Pro Leu Thr Phe Gln Ser Ile Val Gln Phe Lys Ala Asn
            690                 695                 700

Asp Glu Ser Gln Gly Gly Ser Thr Phe Pro Thr Val Leu Phe Ser Asn
705                 710                 715                 720
```

```
Ser Arg Ser Cys Tyr Ser Asn Gln Leu Tyr His Met Ser Tyr Ile Ile
            725                 730                 735

Leu Val Gln Asn Lys Pro Arg Leu Tyr Lys Ile Pro Phe Thr Thr Val
        740                 745                 750

Ser Ala Ser Met Ser Ser Pro Ser Asp Asn Lys Ala Gly Met Ser Ala
        755                 760                 765

Ser Ser Thr Pro Ala Ser Asp His His Ala Ser Gly Asp His Leu Ser
    770                 775                 780

Pro Arg Ser Val Glu Pro Ser Leu Ser Thr Thr Leu Ser Pro Pro Pro
785                 790                 795                 800

Asn Ala Asn Gly Ala Gly Asn Lys Phe Arg Ser Thr Leu Trp His Ala
                805                 810                 815

Lys Gln Ile Cys Gly Ile Ser Ile Asn Asn Asn His Asn Ser Asn Leu
            820                 825                 830

Ala Ala Lys Val Asn Ser Leu Gln Pro Leu Trp His Ala Gly Lys Leu
        835                 840                 845

Ile Ser Ser Lys Ser Glu His Thr Gln Leu Leu Lys Leu Leu Asn Asn
    850                 855                 860

Leu Glu Cys Ala Thr Gly Trp Pro Met Asn Trp Lys Gly Lys Glu Leu
865                 870                 875                 880

Ile Asp Tyr Trp Asn Val Glu Glu
            885

<210> SEQ ID NO 3
<211> LENGTH: 2091
<212> TYPE: DNA
<213> ORGANISM: Pichia pastoris

<400> SEQUENCE: 3
atgaggccta caggaatgag tatcgggacg atactatatg caggaattg cactctatgg       60 tctccaatga tacagaatcg caaggagacg ataggatcac aaatgtcccc ggagatcatc     120
acaagtcagc agatgttatg gtcttttttg gtgggtctaa cagcggcagt cggagggttt     180
ctttatggat acgatacagg cgtcattaat agtttactgg aaatgaacta tttcaaaagc     240
aagttcgcaa gcaatgaggc taggtttaca gctgtggaga cttctataat gacagctagt     300
ttatcgctag gtgcttttg tggtgcttta tccgctcctt tgacatcgga tagttgggga     360
agaagatggt ctattattat agccacgctc atattttta acataggcac catcatacaa     420
acagtggcct ataacattgc catgattgct atgggcagat ttatttcagg attggcggtg     480
ggtattattt ctgctgtggt tccgctatat caagctgaag cttccccaaa gaacatcaga     540
ggttccatta tctcgctgta tcaatggtca atcacctggg gactactatg ctcgagtgct     600
gttgctcaag ggactcacga cttgaatgat tccagaagtt ttcggattcc tattgctctc     660
caattctttt ggtcggcact cttaactaca gggatgtatg tgcttccgga gtcaccgcgt     720
tactacgtca gtaaagatca actggataag gctattgcgt ccttatcaag attgaggcgc     780
cttccatggg atagtgagga gttaattgag gagctcatcg agattaaagc tagcagggac     840 tatgaaaaaaa gttttggaga agctcgtctt attgattgct tcagatcatc cccaagtaga     900
cataagcagg gatttagaat tatgactgct actattctac aggcgttaca acagtgttca     960
ggaatcaact ttattttcta ctatggtgtc aacttcttta tgaatacagg tgttgacacc    1020
tcatatttga tgtcctttat cacgtatgct gtcaatgttg tactaacaat cccaggaata    1080
atgctagtgg aggtgattgg aagaagaaaa ctactgttat ctggagccgc tggaatgtct    1140
```

```
gtttccaatt tgattattgg aatagtgggt acagtggcag attccgtgat tgtcaataaa      1200
gtaatgattg cgtttgtgtg ctcattcata gcattctttg cttccacttg gggtccatgt      1260
gtatgggttg tttctggaga atgttttcct ttgtctgtga gacaaaagtc gatggcttta      1320
tcctctgcta caaattggtt tgtgaatttt gtgttcgcat attgtacccc atatttagtg      1380
gacactggta accacacagc agcgctggga accaacatttt tctttatttg gggtggttgt      1440
aactttctgg gactaatttt cacatatttc tgtgtgtatg aaaccaaagg gttacttctg      1500
gaagagattg atctaatgta caaacacagc aagtttgcct ggaaatcctc tgagttcaag      1560
tcaatattgg aaaagagagt actagaaaga aacaatttgc gggaccatga gataggagaa      1620
gtagttgacc cagatcagga tgagggagag gacactccaa ggaaacctaa atcctccaat      1680
ttgtcttcgt cttacggaac ttctagttcg attgatagga ccgattttga tcaagaagct      1740
gaaactgttc cattaccagc cttcgcttct tcagccctct acggtgagaa ttccgaaaat      1800
tttttgccat caactaacac agcaagccac gtaccattcg aaataaaccc atctagcagt      1860
tttccggaag aagatgatgg aattcacgag gaagcggatg agaatcatat gaacaataac      1920
gacccaatgc atgaatctta caattacagc aacagcgacg agctgaaaga tctcatcaat      1980
aatcttcaaa caacacctac agaatcgtca atacgacagc ggtaccaagg atatcaggac      2040
gataacgact ccgatgagtc gtcgcaaaac tcatacacta tgcaggcata a              2091
```

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
cgagctcaga tctttttttgt agaaatgtc                                       29

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
gactagtgca caaacgaagg tctc                                             24

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
ccggaattct agtcacggat tgcttc                                           26

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7

```
acatgcatgc gttcccaata gatttcacaa                                        30

<210> SEQ ID NO 8
<211> LENGTH: 630
<212> TYPE: DNA
<213> ORGANISM: Pichia pastoris

<400> SEQUENCE: 8
atgagttttc aagtctacaa catggtgtcc ttgccagcac cgcaagcaac atcattctcc        60
caacatccga aacttccaac attggaagtg atacaacggc caccactcac tggaagacat       120
ggcattcacg aagaagagat caagctacct tcctttagat ctttactggc tagtgcgggc       180
actgccgctg ctcttgaata tcccccagg attcaacccc aatttgcaac aggggcacct        240
gcacctgagc aagcatttta tcagccccta ataccgtgg gagtcacgag cccaacatt         300 cacacctcca tcactccacc actggaggcg caggacctcc ctcaccaaca aaagtttatg       360
gaaccatttg cgtccttccc caatacagta gtgtcttcta cacccaacac agccatcaga       420
aaatacaagt gcaagatctg cgagaggtct ttcacaacgt cgggccactt agctcgtcac       480
acacgtattc acactggtga aaagaagcat gagtgtcctt cgaaggctg ttctgctagg        540 ttcagccgtc aggataactg catgcaacat tacaagacgc atgttaatac caagtcgaaa       600
cgaaagagat ctagattgag aagtaaatag                                        630

<210> SEQ ID NO 9
<211> LENGTH: 1329
<212> TYPE: DNA
<213> ORGANISM: Pichia pastoris

<400> SEQUENCE: 9
accactgcct atcccaacgc acgtgtggca agtgtcagat cgtcggggga ctctgtgggt        60
gatatcaaag tgggctccag gaagtccgcg gagtcttcta acgcaaactc cagctccagc       120
tctaaaaaat cagagttatc acgccccctac caatgtccca tgtgtgaaaa ggctctccac       180
agattagagc atcaaacaag acacatacgg actcacacgg gtgagaagcc ccaccactgt       240
aattatcccg gctgtttcaa gaagttttca aggtcggatg agttgaccag acattccaga       300
atacacaaca acccaaaccc gaggaaaagg gggccaggtg ttgtcccaa gaagactcct         360 agaccaaaga tggcaggcaa gtcagcctca tatagtgacg agggcaacta ctcttttaggc      420 gaaggccatc agcagtttta cggcagtgat gacgcttcct ctttcccgtt ggtgtcgatt       480
ccaactgcag cagcaactac cacggtggga aaaccaacaa ccccaactcc gagctcaaag       540
tcgtctcaga gccagacagc tgaggccaag ttcaaccctc taagaagtgc gtctactctg       600
agcatcaact gctggctac tgctgcctct caggaactac aagagttaag ggctgcagag        660
gaaaactctt caagattgca acaagtaaaa tctctacctt cgttaactca atacttcatt       720
gcttcggaag actcctctca tggtggaaac cctccgttat ctcatccgaa gccattcagc       780
agtctaagcg gacttaaaag aatgacccca ataaaccctt cttcttcttc ctcttcgccc       840
ggaggtgttt caatcaacaa atcaatatct gttacttcgt tgactcgaac cttttccaac       900
acagagattg ctgacgaatt cactactcct ccgacaatgt gaaaaaatc ccgaccaaat        960 tcgcctgtgc tcacaggacg atctccaacg acttttcaac aataccaaca atcacagcat      1020
acatctaact tggcacagca gcaatctaag ggtaactttc ctccatccca tattgattcc      1080
aaggtttcat cagcggctct gcatctttta ggacttgggc tgaaccatgc cactcctgaa      1140 gtcaccccctt tgcaaaccccc tgcagtgtct cccaaactct ttccaaaatc cgtttccaat    1200
```

```
aatagcttgg agacacttca caaagctttg gatgagacca ctgaagcaga gaacctccaa    1260
agcacagcac taccttctct gagctctcta aatttacctt caacctctct ggaaaatcaa    1320
gaaaagaaa                                                            1329
```

<210> SEQ ID NO 10
<211> LENGTH: 1359
<212> TYPE: DNA
<213> ORGANISM: Pichia pastoris

<400> SEQUENCE: 10

```
actactgctc ccccaacgaa gcccaatgat aggccctacc agtgcccccat gtgcgacaag     60 gccttccacc ggttggaaca tcaaacagga cacattagaa cacacacagg ggaaaaacct    120 caccccttgca cgttccctgg atgcccaaag aagttttcca ggtctgatga attgaccaga    180
cacttgagga tacacacaaa cccaactgtg agaagggca gaagaagaa gcggaaggac     240 gaagaacaag ctgtggagtt gccacctcag aataacgagg tacatctcgt tcccatgggg    300
aacgatcaaa tgggacaacc aatatacacg caggcggttc ctgtttattg ggttccatct    360
ggtgctgcaa acggcgaaca aggccagtat ttgatgcctc cgctttttc cttacaacca    420 agacaggtga tggcagggac ttctcaaacc agtttgaatg gtgtagatgc tcaacaacag    480
cagcagcagc agcagcagca gcaacaacaa caacaacaac aacaacaaca accacagcaa    540
caaccacagc aacaaccgcc actgcaacca caaccacttc aaccacaacc acaggcccag    600
caacaatttg gatttgctca agatcaaaga aacctggcac ccgctaatca gcaacagcac    660
agattctccc caccattttc tgcatcttca aggacccttt cagccaattc attgttttct    720
ctcaactcaa atggatccac gccttcaggg tcatatcaac agttgaactc tttatctctt    780
ttacacagaa tcactccaat caggactcca agcagtaata gcctgttgac aaaatctaat    840
aaccagtcga tgacatcaat agtcacgttg agcgaccaac aacaggattt tgtttccaga    900
aaaaagtcaa gacccaactc accaacagtt ccaaactctc caacaatttc aaacttggtc    960
tcgcccgctg atacgccttt aactactccg ttgcaatcgc ctacactgaa gcccgcaatg   1020
cccagcaacg tacaacttcc accaataaga tcactgttaa atttggaaga acttccctcg   1080
gaaccattgc agcaaccagc caatgtctct actgacaata agtgaagac aatgttgaac   1140 aaatcttcgt ccaacgtcac tttgagtaaa tcgtttttctt cacaagacat tcgtctgggg   1200
accaagagaa agtctgatac caacctctct gcattagatt ctaccaatgc tattcgcaag   1260
cctgccctat caccgttggc tcctctgtca gtctcatcag atcgatttac aagagaaag   1320 aacaacttca cgataggcaa tatcatgaac tcggactct                           1359
```

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11

```
ccggaattct agtcacggat tgcttc                                          26
```

<210> SEQ ID NO 12
<211> LENGTH: 31
<212> TYPE: DNA
<213> ORGANISM: Artificial Sequence
<220> FEATURE:

<223> OTHER INFORMATION: Primer

<400> SEQUENCE: 12
cgcggatcca gtctgaaata ggctcagaca t                                   31

<210> SEQ ID NO 13
<211> LENGTH: 32
<212> TYPE: DNA
<213> ORGANISM: Artificial Sequence
<220> FEATURE:
<223> OTHER INFORMATION: Primer

<400> SEQUENCE: 13
acgcgtcgac atgcctattg aacaagacta tt                                  32

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
acatgcatgc gttcccaata gatttcacaa                                     30

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
cgagctcctg tgcctattac cccccTT                                        27

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
tcccccggga acagataacc aaaacggacg                                     30

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
gctctagagt atttatttac ggattgga                                       28

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
acatgcatgc caccactttt tgaatctcgg                                     30

```
<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
tcccccggga gcttgccttg tccccgccg                                              29

<210> SEQ ID NO 20
<211> LENGTH: 28
<212> TYPE: DNA
<213> ORGANISM: Artificial Sequence
<220> FEATURE:
<223> OTHER INFORMATION: Primer

<400> SEQUENCE: 20
gctctagatc gacactggat ggcggcgt                                               28

<210> SEQ ID NO 21
<211> LENGTH: 40
<212> TYPE: DNA
<213> ORGANISM: Artificial Sequence
<220> FEATURE:
<223> OTHER INFORMATION: Primer

<400> SEQUENCE: 21
tccaatccgt aaataaatac tcgacactgg atggcggcgt                                  40

<210> SEQ ID NO 22
<211> LENGTH: 40
<212> TYPE: DNA
<213> ORGANISM: Artificial Sequence
<220> FEATURE:
<223> OTHER INFORMATION: Primer

<400> SEQUENCE: 22
acgccgccat ccagtgtcga gtatttattt acggattgga                                  40
```

METHOD OF ELIMINATING DEPENDENCE OF METHANOL INDUCED PROMOTER ON SINGLE METHANOL CARBON SOURCE

CROSS REFERENCE TO RELATED APPLICATIONS

This application is a U.S. National Phase Application under 35 U.S.C. 371 of International Application No. PCT/CN2012/084642 filed on Nov. 15, 2012 and published in Chinese as WO 2014/008729 on Jan. 16, 2014. This application is based on and claims the benefit of priority from Chinese Patent Application No. 201210196862.7 filed Jul. 12, 2012. The entire disclosures of all of the above applications are incorporated herein by reference.

TECHNICAL FIELD

The invention relates to the field of bioengineering; more particularly, the invention relates to a method for eliminating the dependence on methanol as the single carbon source of a methanol inducible promoter for driving the expression of an exogenous polypeptide.

TECHNICAL BACKGROUND

Methylotrophic yeast (including *Pichia, Hansenula, Candida, Torulopsis* et al.) expression systems have been wildly used in industrial production and pharmacy for their efficient ability of expressing an exogenous polypeptide. It is characterized that these systems have promoters (AOX1 promoter, DHAS promoter, FDH promoter, MOX promoter, AOX2 promoter, ZZA1, PEX5-, PEX8-, PEX14-promoter et al.) which can be induced efficiently by methanol, and these promoters depend on methanol strictly while other carbon sources such as glucose, glycerol et al. will suppress the expression of these promoters.

With the outbreak of the oil crisis, the cost of producing simple-cell proteins with methanol increases. So many exogenous polypeptides are expressed with methylotrophic yeast expression systems for their incomparable advantages over other expression systems as follows: simple genetic manipulation, high expression of an exogenous polypeptide, with intracellular or secretory expression; the inheritance of an exogenous polypeptide is stable; as an eukaryotic expression system, having subcellular structures of eukaryotes, having the function of post-translational modification such as glycosylation, fatty acylation and protein phosphorylation.

As the usage scope increases, there are many problems occurring during the actual fermentation scale-up: (1) the promoter used in the expression needs to be induced by methanol, and special explosion-proof design is necessary in large scale industrial fermentation for methanol is toxic and inflammable; (2) methanol fermentation consumes large amount of oxygen, and it is difficult to meet the need for oxygen by just increasing air ventilation volume and raising rotation rate, so the pure oxygen is necessary, the oxygen desired in methanol metabolism is 3 to 4 times the amount of oxygen desired wherein glucose is the carbon source. The more methanol is consumed, the more pure oxygen is desired which bring about a great trouble to the actual industrialization. Furthermore, the more methanol is consumed, the more heat is produced which increases requirement of the cooling ability of the instrument; (3) methanol is a petrochemical product which is not suitable for some food additives production; (4) methanol metabolism will produce $H_2O_2$, which leads to the hydrolysis of the expressed polypeptides.

Therefore, if a method for expressing by a methanol inducible promoter without methanol so that the efficient transcription of a methanol inducible promoter will not depend on methanol and other carbon sources can be used to induce the expression of the promoter is obtained, it will be a positive significance for expressing exogenous polypeptides efficiently without methanol.

THE CONTENT OF THE INVENTION

One object of the invention is to provide a method for eliminating the dependence on methanol as the single carbon source of a methanol inducible promoter for driving the expression of an exogenous polypeptide with the methanol inducible promoter.

Another object of the invention is to provide a recombinant methylotrophic yeast, which can utilize the methanol inducible promoter which has eliminated the dependence on methanol as the single carbon source for driving the expression of an exogenous polypeptide.

In the first aspect of the invention, a method for eliminating the dependence on methanol as the single carbon source of a methanol inducible promoter for driving the expression of an exogenous polypeptide encoding gene is provided, which comprises:

(1) Providing a methylotrophic yeast, said methylotrophic yeast comprises:

Expression cassette 1, which expresses exogenous Mit1 polypeptide; and

Expression cassette 2, which comprises a methanol inducible promoter and an exogenous polypeptide encoding gene which is operably linked to the promoter;

(2) Culturing the methylotrophic yeast of (1) under the conditions wherein there is no methanol or methanol is not the only carbon source.

In a preferred example, said Mit1 polypeptide is a transcription activator which allows a methanol inducible promoter to express an exogenous polypeptide without the dependence on methanol.

In another preferred example, the function of said Mit1 polypeptide is to activate the methanol inducible promoter desired in methanol metabolism.

In another preferred example, said Mit1 is PpMit1.

In another preferred example, the expression cassette 2 can be included in the methylotrophic yeast as single copy or multiple copies, for example, 1 to 20 copies, such as 15, 10, 8, 6, 5, 3, 2 copies.

In another preferred example, the methanol inducible promoter includes but not limited to: AOX1 promoter, DHAS promoter, DAS promoter, FDH promoter, FMDH promoter, MOX promoter, AOX2 promoter, ZZA1, PEX5-, PEX8-, PEX14-promoter, PMP20 promoter, PMP47 promoter, AOD1 promoter, AOD2 promoter.

In another preferred example, the methylotrophic yeast includes but not limited to: *Pichia, Hansenula, Candida, Torulopsis*; preferably, the *Pichia* includes but not limited to: GS115, the *Pichia* wherein the MIG1 and MIG2 gene unexpressed (Δmig1Δmig2), the *Pichia* wherein the NRG1, MIG1 and MIG2 gene unexpressed (Δmig1Δmig2Δnrg1), or the *Pichia* wherein the HXS1 gene unexpressed.

In another preferred example, the Mit1 polypeptide is selected from the group consisting of:

(a) a polypeptide with an amino acid sequence as set forth in SEQ ID NO: 2; or (b) a polypeptide derived from (a) by substitution, deletion or addition of one or more (such as 1 to 30, preferably 1 to 20, more preferably 1 to 15, more preferably 1 to 10, even more preferably 1 to 5 or 1 to 3) residues in the amino acid sequence of SEQ ID NO: 2 and having the ability to induce a methanol inducible promoter to express an exogenous polypeptide with carbon sources other than methanol;

(c) a polypeptide derived from (a), having more than 70% (preferably more than 80%, more preferably more than 90%, more preferably more than 95%, more preferably more than 98%, such as 99% or more) identity to the amino acid sequence defined in (a) and having the ability to induce a methanol inducible promoter to express an exogenous polypeptide with carbon sources other than methanol.

In another preferred example, the encoding gene of the Mit1 polypeptide has a NCBI Reference Sequence of XM_002493021.1.

In another preferred example, the encoding gene of the Mit1 polypeptide has a nucleotide sequence as set forth in SEQ ID NO: 1.

In another preferred example, the encoding gene of the Mit1 polypeptide is induced to express in the presence of methanol and not express in the presence of carbon sources such as glycerol, glucose, and the like.

In another preferred example, the expression cassette 1 comprises: a promoter and the encoding sequence of Mit1 polypeptide which is operably linked to the promoter; preferably, the promoter includes but not limited to: a constitutive promoter, an inducible promoter, a tissue or organ specific promoter, a temporal and spatial specificity expression promoter.

In another preferred example, the promoter included in the expression cassette 1 includes but not limited to: GAP promoter, PGK1 promoter, MIT1 promoter and any promoter which overexpresses MIT1.

In another preferred example, said expression cassette 1 is included in the methylotrophic yeast as single copy or multiple copies, for example, 1 to 20 copies, such as 15, 10, 8, 6, 5, 3, 2 copies.

In another preferred example, glycerol/glucose containing yeast culture medium is used in step (2).

In another aspect of this invention, use of the Mit1 polypeptide or the encoding gene thereof for eliminating the dependence on methanol as the single carbon source of a methanol inducible promoter for driving the expression of an exogenous polypeptide encoding gene is provided.

In another aspect of this invention, a recombinant methylotrophic yeast is provided, the methylotrophic yeast comprises:

Expression cassette 1, which can express exogenous Mit1 polypeptide; and

Expression cassette 2, which comprises a methanol inducible promoter and an exogenous polypeptide encoding gene which is operably linked to the promoter.

In a preferred example, the methylotrophic yeast includes but not limited to: Pichia, Hansenula, Candida, Torulopsis; preferably, the Pichia includes but not limited to: GS115, the Pichia wherein the MIG1 gene and MIG2 gene unexpressed (Δmig1Δmig2), the Pichia wherein the NRG1 gene, MIG1 gene and MIG2 gene unexpressed (Δmig1Δmig2Δnrg1), or the Pichia wherein the HXS1 gene unexpressed.

In a preferred example, said MIG1 gene has a nucleotide sequence as set forth in SEQ ID NO: 9;

Said MIG2 gene with a nucleotide sequence as set forth in SEQ ID NO: 10; or

Said HXS1 gene with a nucleotide sequence as set forth in SEQ ID NO: 3.

Said NRG1 gene with a nucleotide sequence as set forth in SEQ ID NO: 8 (NCBI Reference Sequence: XM_002493138.1).

According to the disclosed content herein, other aspects of the invention are apparent to those skilled in the art.

DESCRIPTION OF DRAWINGS

FIG. 1 shows the plasmid profile of pGAPZαA.

FIG. 2 shows the plasmid profile of vector pAG32.

FIG. 8 shows the geometric mean fluorescence intensity of GFP of the samples by flow cytometry, and the samples are obtained from wild and Δmig1Δmig2-MIT1 and Δhxs1-MIT1 strains cultured in non-methanol or methanol containing culture medium.

FIG. 9 shows the plasmid profile of vector pPIC3.5K.

FIG. 10 shows the plasmid profile of vector pUC18.

FIG. 11 shows the results of Aox enzyme activity assay of the total protein after Bradford quantity, and the total protein is obtained from wild and Δmig1Δmig2Δnrg1-MIT1 strains of logarithmic phase cultured in non-methanol or methanol containing culture medium.

DETAILED DESCRIPTION OF THE PREFERRED EMBODIMENTS

Figure 3:
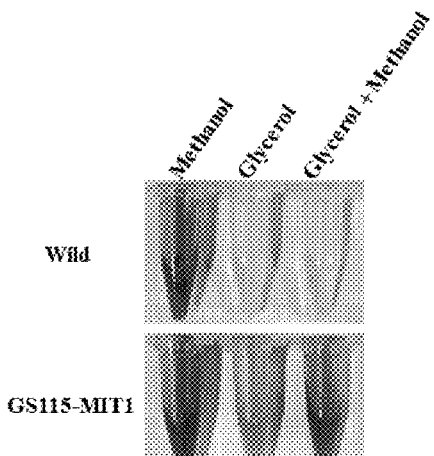
FIG. 3 shows the results of Aox developing of wild and GS115-MIT1 which are cultured in non-methanol or methanol containing (glycerol+methanol) culture medium.

In order to overcome the limitation of the dependence on a methanol inducible promoter on methanol in fermentation, after thorough study, the inventor discloses a method for eliminating the dependence on methanol as the single carbon source of methanol inducible promoter by increasing the intracellular expression of Mit1 (Methanol Induced Transcription Factor 1) polypeptide in the methylotrophic yeast to activate the expression of the promoter induced by the single carbon source of methanol in the methanol metabolism, so that the promoter can also express exogenous polypeptides without methanol.

Terms

As used herein, a "promoter" refers to a nucleic acid sequence generally present in the upstream (5') of the encoding sequence of target gene, which can direct the transcription of nucleic acid sequence into mRNA. Generally, a promoter or a promoter region provides recognition sites for RNA polymerase and other factors desired for correctly starting transcription. The promoter or promoter region comprises its active variants; such variants can be naturally occurring allelic variants or non-naturally occurring variants. Said variants include substitution variants, deletion variants and insertion variants.

As used herein, the "methanol inducible promoter" is the promoter of an enzyme associated with methanol metabolism. In the prior art, these promoters can regulate the expression of exogenous polypeptides by adding methanol to the growth culture medium. Said "methanol inducible promoter" can be separated from yeasts by those skilled in the art with common methods.

As used herein, the "induced with methanol as the single carbon source" means that a promoter is induced with methanol as the single carbon source to drive the expression of a gene which is operably linked to the promoter, and cannot drive the expression of a gene which is operably linked to the promoter under the condition wherein methanol is not the only carbon source (such as methanol+glucose). The "eliminating the dependence on methanol as the single carbon source" means that a promoter can drive the expression of a gene which is operably linked to it under the condition wherein methanol is not the only carbon source (such as methanol+glucose, or glucose, or glycerol). The "induced with methanol not as the single carbon source" means that a promoter is induced with at least one carbon source other than the carbon source of methanol.

As used herein, the "constitutive promoter" refers to a class of promoters wherein there is no significant difference in the expression of genes in different tissues or organs and development phases under the regulation thereof.

As used herein, the "inducible promoter" can induce rapidly the "open" and "close" or "high" and "low" of the gene transcription according to the certain cell growth phases or certain growth environment. Based on the sources, the inducible promoters can be divided into naturally occurring promoters and artificial promoters.

As used herein, the "tissue or organ specific promoter" refers to a promoter, wherein the gene transcription which only occurs in certain tissues or organs.

As used herein, "exogenous" or "heterologous" refers to the relationship between two or more nucleotide or protein sequences from different sources. For example, if a promoter and a target gene are not naturally linked, the promoter is exogenous to the target gene. When certain sequence is inserted to a cell or organism, said sequence is "exogenous" to said cell or organism.

As used herein, the "expression cassette" refers to a gene expression system comprising all the necessary elements desired for the expression of target polypeptides (such as exogenous polypeptides or Mit1 polypeptide herein), and the system generally comprises the following elements: a promoter, a gene sequence encoding a polypeptide, a terminator; furthermore, the system may optionally comprise a signal peptide encoding sequence and the like. These elements are operably linked.

As used herein, the "methylotrophic yeast" refers to yeast which can use methanol as the only carbon source, including a yeast from *Hansenula, Pichia, Torulopsis, Candida*, et al.

As used herein, the "operably link" refers to the functional spatial arrangement of two or more nucleic acid regions or nucleic acid sequences. For example, the promoter is arranged in the special position relative to the nucleic acid sequence of the target gene, so that the transcription of the nucleic acid sequence is directed by the promoter region and thereby the promoter region is "operably linked" to the nucleic acid sequence.

As used herein, term "strict condition" refers to: (1) hybridizing and eluting at lower ion strength and higher temperature, such as 0.2×SSC, 0.1% SDS, 60° C.; or (2) adding denaturant during hybridizing, such as 50% (v/v) formamide, 0.1% calf serum/0.1% Ficoll, 42° C. and the like; or (3) the hybridization will not occur unless the identity between two sequence is at least more than 50%, preferably more than 55%, more than 60%, more than 65%, more than 70%, more than 75%, more than 80%, more than 85% or more than 90%, more preferably more than 95%.

As used herein, the "comprising", "having" or "including" include "mainly consisting of", "essentially consisting of" and "consisting of"; "mainly consisting of", "essentially consisting of", and "consisting of" are the subordinate concept of "comprising", "having" or "including".

Mit1 Polypeptide

The present invention discloses use of a Mit1 polypeptide in eliminating the dependence on methanol as the single carbon source of a methanol inducible promoter for driving the expression of an exogenous polypeptide with said promoter. In the study of the promoters which drive the expression of exogenous polypeptides by methanol (methanol inducible promoters), the inventor has unexpectedly found that the Mit1 polypeptide can eliminate the dependence on methanol as the single carbon source of a methanol inducible promoter so that the promoter can express an exogenous polypeptide with methanol as the non-single carbon source or with a carbon sources other than methanol.

The present invention further comprises the fragments, derivatives and analogs of the Mit1 polypeptide. As used herein, terms "fragment", "derivative" and "analog" refer to a polypeptide which keeps the same biological function or activity as the MIT1 polypeptide. The polypeptide fragments, derivatives or analogs of the invention can be (i) a polypeptide with one or more conservative or non-conservative amino acid residues (preferably conservative amino acid residues) substituted, and such amino acid residue substitution may not be encoded by genetic code, or (ii) a polypeptide in which one or more amino acid residues have a substituent group, or (iii) a polypeptide formed by fusing mature polypeptide with another compound (for example, a compound prolonging the half-life of the polypeptide, e.g. polyethylene glycol), or (iv) a polypeptide with additional amino acid sequence fused therein (such as leader sequence, or secreting sequence, or a sequence used to purify the polypeptide, or a polypeptide original sequence, or a fused polypeptide). According to the definition herein, these fragments, derivatives and analogs are known to a person skilled in the art.

As used herein, term "Mit1" refers to a polypeptide as set forth in SEQ ID NO: 2 which has the function of inducing a methanol inducible promoter to drive the expression of an exogenous polypeptide with a carbon source other than methanol. Such term further comprises the variants of SEQ ID NO: 2 which have the function of inducing a methanol inducible promoter to drive the expression of an exogenous polypeptide with a carbon source other than methanol. These variants include but not limited to: deletion, insertion and/or substitution of a plurality of (generally 1-50, preferably 1-30, more preferably 1-20, most preferably 1-10, further more preferably 1-8 or 1-5) amino acids, and addition or deletion of one or more (generally within 20, preferably within 10, more preferably within 5) amino acids at the C-terminus and/or N-terminus. For example, in the art, when the substitution is carried out by amino acids with similar properties, or similar amino acids, the function of the protein is usually not changed. As another example, adding or deleting one or more amino acids at the C-terminus and/or N-terminus usually does not change the function of the protein.

Variant forms of polypeptides include: homologous sequences, conservative variants, allelic variants, natural mutants, induced mutants, the protein encoded by DNA which can hybridize with DNA of Mit1 protein under high or low stringency conditions, as well as the polypeptide or protein obtained by utilizing anti-serum of Mit1 protein. The present invention also provides other polypeptides, such as the fusion protein containing Mit1 protein or fragment thereof.

The present invention further provides Mit1 polypeptides or polypeptide analogs. The difference between these analogs and natural Mit1 protein can be a difference in amino acid sequence, also can be a difference not affecting modified forms of the sequence, or both. These polypeptides comprise natural or induced genetic variants. Induced variants can be obtained by various methods, such as by radiation or being exposed in mutagen to achieve random mutagenesis, or by site-directed mutagenesis or other known molecular biological methods. Analogs further comprise analogs with residues other than natural L-amino acids (such as D-amino acid), and analogs with non-naturally occurring or artificial amino acids (such as β, γ-amino acid). It should be understood that the polypeptides of the invention are not limited to the representative polypeptides above.

The present invention further provides the polynucleotide sequences encoding a Mit1 polypeptide or the conservative variant polypeptides thereof.

The polynucleotides of the invention can be in the form of DNA or RNA. The DNA includes cDNA, genomic DNA or artificial DNA. The DNA can be single chain or double chain. The DNA can be the coding strand or the non-coding strand. The encoding region sequence of mature polypeptides can be the same sequence or degeneration variants of SEQ ID NO: 1. As used herein, As used therein, "a degeneration variant" refers to a nucleic acid molecule that encodes a protein having the sequence of SEQ ID NO: 2 with a nucleotide sequence different from the coding sequence as set forth in SEQ ID NO: 1.

The present invention also relates to variants of above-mentioned polynucleotides which encode polypeptides or polypeptide fragments, analogs and derivatives having the same amino acid sequences as the present invention. These polynucleotide variants can be naturally occurring allelic variants or non-naturally occurring variants. These nucleotide variants include substitution variants, deletion variants, and insertion variants. As known in the art, allelic variant is an alternate form of polynucleotide, it may be one or more nucleotide substitutions, deletions or insertions, but will not substantially alter its polypeptide-encoding function.

The present invention further relates to polynucleotides which are homologous with the polynucleotides above, they have at least 50%, preferably at least 60%, more preferably at least 70%, more preferably at least 80%, more preferably at least 90%, more preferably at least 95%, even more preferably at least 98% or 99% identity to the polynucleotides above. The proteins encoded by these polynucleotides also have the same function with the proteins encoded by the above polypeptides to induce a methanol inducible promoter to drive the expression of exogenous polypeptides.

The present invention further relates to a polynucleotide which hybridizes with the above sequence and the identity between the two sequences is at least 50%, preferably at least 70%, more preferably at least 80%. The invention particularly directs to a polynucleotide which hybridizes with the polynucleotide of the invention under strict conditions.

The full-length sequence of Mit1 polypeptide of the present invention or fragments thereof can usually be obtained by PCR amplification method, recombinant method or artificial synthesis. As to PCR amplification method, the sequences of interests can be amplified by designing primers according to the related nucleotide sequence disclosed in the present invention, especially the open-reading frame, and using a commercially available cDNA library or a cDNA library prepared according to any of the conventional methods known in the art as a template. For an excessively long sequence, typically, two or more PCR amplifications are needed, and then, the fragments obtained in the amplifications are ligated together in a correct orientation.

In the present invention, the polynucleotide sequence encoding Mid polypeptide can be inserted into a recombinant expression vector. The term "recombinant expression vector" refers to bacterial plasmid, bacteriophage, yeast plasmid, plant cell virus, mammalian cell virus, or other vectors. In short, any plasmid and vector may be used as long as it can be replicated and stable in the host. An important feature of the expression vector is typically containing an origin of replication, promoter, marker gene and translation control elements.

The common methods in the art can be used to construct an expression vector containing a Mit1 polypeptide encoding DNA sequence and a suitable transcription/translation regulatory signal. Such methods include DNA recombination in vitro, DNA synthesis, recombination technique in vivo and the like. Said DNA sequences can be effectively connected to the appropriate promoter in the expression vector to direct DNA synthesis. An expression vector can further comprise a ribosome binding site used in translation initiation and a transcription terminator.

Furthermore, an expression vector preferably contains one or more marker gene to provide transformed host cells phenotypic traits for selection, such as dihyrofolate reductase, neomycin resistance and green fluorescent protein (GFP) in the eucaryote cell culture.

A vector containing appropriate DNA sequence and promoter or regulatory sequence above can be used to transform host cells for the expression of proteins.

The methods for increasing the expression of Mit1 polypeptide is known in the art. For example, an expression construct carrying Mit1 polypeptide encoding gene can be transformed into yeast cells to make them express Mit1 polypeptide; or the expression of Mit1 polypeptide can be increased by using a strong promoter; or the expression of Mit1 polypeptide can be increased by using an enhancer.

Methanol Inducible Promoter

In the common methods, the expression of exogenous polypeptides driven by the methanol inducible promoter is dependent on adding methanol to the culture medium. However, the inventor discloses a method for eliminating the dependence on methanol of a methanol inducible promoter.

Those skilled in the art are familiar with a methanol inducible promoter which can be separated from yeast by common methods. As methanol inducible promoters have essentially same work mechanism and principle, there is no particular limit to the kinds of methanol inducible promoters. For example, the methanol inducible promoters include but not limited to: AOX1 promoter, DHAS promoter (or DAS promoter), FDH promoter (or FMDH promoter), MOX promoter, AOX2 promoter, ZZA1, PEX5-, PEX8-, PEX14- promoter, PMP20 promoter, PMP47 promoter, AOD1 promoter, AOD2 promoter.

The invention further comprises a promoter with an identity of at least 70%, preferably at least 80% (e.g. 85%, 90%, 95%, 96%, 97%, 98%, or 99%) to the nucleotide sequence of the above promoters. These promoters are strictly conservative in the essential sites for transcription initiation and transcription start sites. The invention particularly relates to a polynucleotide which can hybridize with the nucleotide sequence of the methanol inducible promoter of the invention under strict conditions, and such polynucleotide also has the function with a wild methanol inducible promoter.

Method for Eliminating Dependence on Methanol as the Single Carbon Source of a Methanol Inducible Promoter for Driving the Expression of an Exogenous Polypeptide Encoding Gene The invention further provides a method for eliminating dependence on methanol as the single carbon source of a methanol inducible promoter for driving the expression of an exogenous polypeptide encoding gene, comprising:

(1) Providing a methylotrophic yeast, the methylotrophic yeast comprises:

Expression cassette 1, which expresses an exogenous Mit1 polypeptide; and expression cassette 2, which comprises a methanol inducible promoter and an exogenous polypeptide encoding gene which is operably linked to the promoter;

(2) Culturing the methylotrophic yeast in (1) under the conditions wherein there is no methanol or methanol is not the only carbon source.

The expression cassette 1 and expression cassette 2 can be present in the same expression vector or different expression vectors.

The expression cassette 1 can be included in the methylotrophic yeast as single copy or multiple copies, for example, 1 to 20 copies, such as 15, 10, 8, 6, 5, 3, 2 copies. The expression cassette 2 can be included in the methylotrophic yeast as single copy or multiple copies, for example, 1 to 20 copies, such as 15, 10, 8, 6, 5, 3, 2 copies.

In the expression cassette 1, a promoter and a Mit1 polypeptide encoding gene which is operably linked to the promoter is included. It should be understood that any promoter which allows the recombinant expression of a Mit1 polypeptide in a methylotrophic yeast can be used in the invention. It is not limited to a constitutive promoter, an inducible promoter or a specific promoter. Those skilled in the art may make suitable selection according to the desired purpose, for example, an inducible promoter can be selected to regulate the expression of Mit1 polypeptide under some conditions. Preferably, in expression cassette 1, the promoter comprises: GAP promoter, PGK1 promoter, MIT1 promoter and any promoter which allows the overexpression of MIT1.

In step (2), "conditions wherein there is no methanol" is easy for those skilled in the art to establish, i.e. it is common knowledge for those skilled in the art to add other kinds of carbon sources other than methanol in the common methylotrophic yeast medium, for example, such carbon sources are not limited to: glycerol, glucose, starch (including starch hydrolysate, tapioca starch, corn starch, cellulose hydrolysate, et al.), sucrose, maltose and the like. Preferably, glycerol and/or glucose are used as the carbon source of yeast culture medium. Similarly, "conditions wherein methanol is not the only carbon source" is also easy for those skilled in the art to establish.

Recombinant Methylotrophic Yeast

Based on the novel findings of the invention, a recombinant methylotrophic yeast is provided, the methylotrophic yeast comprises: expression cassette 1, which can express an exogenous Mit1 polypeptide; and expression cassette 2, which comprises a methanol inducible promoter and an exogenous polypeptide encoding gene which is operably linked to the promoter. Additionally, the expression cassette 1 and expression cassette 2 can be in the same expression vector or different expression vectors.

Any methylotrophic yeast can be used in the invention to construct the recombinant methylotrophic yeast above. For example, the methylotrophic yeast includes but not limited to: *Pichia*, *Hansenula*, *Candida*, *Torulopsis*; preferably, the *Pichia* comprises: GS115, the *Pichia* wherein the MIG1 gene and MIG2 gene unexpressed (Δmig1Δmig2), the *Pichia* wherein the NRG1 gene, MIG1 gene and MIG2 gene unexpressed (Δmig1Δmig2Δnrg1), or the *Pichia* wherein the gene HXS1 unexpressed.

According to the embodiments of the invention, four strains which can induce AOX1 promoter to express an exogenous polypeptide with a carbon source other than methanol are provided, they are GS115-MIT1, Δmig1Δmig2-MIT1, Δhxs1-MIT1 and Δmig1Δmig2Δnrg1-MIT1. Transcription Factor MIT1 is overexpressed in *Pichia* wild strain GS115, *Pichia* double deleted strain Δmig1Δmig2, *Pichia* deleted strain Δhxs1 and *Pichia* triple deleted strain Δmig1Δmig2Δnrg1 respectively to construct gene overexpression strain GS115-MIT1, Δmig1Δmig2-MIT1, Δmig1Δmig2Δnrg1-MIT1 and Δhxs1-MIT1. After Aox1 enzyme activity assay, it is found that glycerol can induce the expression of the AOX1 promoter of GS115-MIT1, glycerol or glucose both can induce the expression of the AOX1 promoter of Δmig1Δmig2-MIT1, Δhxs1-MIT1 and Δmig1Δmig2Δnrg1-MIT1. When the promoter is AOX1, the induced expression amount of the green fluorescent protein (GFP) is detected by flow cytometry.

Among the Δhxs1 strains, an encoding region of HXS1 (GenBank accession number: 8197942) is deleted which is highly similar with *Saccharomyces cerevisiae* hexose inductor Snf3/Rgt2.

The present invention will be further illustrated in combination with the following examples. It should be understood that these examples are for illustrating the present invention, but not for limiting the scope of the present invention. The experimental method in which the specific conditions are not specifically indicated in the following examples generally is performed according to the conventional conditions, such as those described in Sambrook et al., Molecular Cloning: A Laboratory Manual (New York: Cold Spring Harbor Laboratory Press, 2002), or according to the conditions recommended by the manufacturer. Unless otherwise specifically indicated, the percent and part are calculated based on weight.

Materials

The methods for extracting the *Pichia* total protein refer to the Manual of Extraction of Yeast Protein provided by Cold Spring Harbor Company.

The tool enzymes used herein are all purchased from TaKaRa Biological Company (Da lian, China), the specific reaction conditions and methods all refer to its instructions.

The following commercial plasmids and strains are used in gene clone and protein expression: Plasmid pGAPZαA, Plasmid pPIC3.5k, *E. coli* Top10, *Pichia* strain GS115, which are purchased from Invitrogen.

Plasmid pAG32 is obtained from Plasmid pRDM054 by deleting the $P_{AOX1}$-BFP-SKL expression system at the restriction site Bgl II of pRDM054; Plasmid pRDM05 is obtained from University of California at San Diego.

YPD medium: 2% peptone, 1% yeast powder, 2% glucose, 2% agar powder; YNB medium: 0.67% YNB; MGY medium: 1% glycerol, 0.67% YNB; YND liquid medium: 1% glucose, 0.67% YNB.

When above mediums are formulated, glucose is sterilized by autoclaving at 115° C. for 20 min, methanol is added when used. Other ingredients are sterilized by autoclaving at 121° C. for 20 min. 2% agar powder is added to form a solid medium.

Example 1

The Expression of *Pichia* Strain GS115-MIT1 with Glycerol Inducible AOX1 Promoter 1. Construction of PpMIT1 Overexpression Plasmid PpMIT1 gene (SEQ ID NO: 1, gene full length: 2667 bp) was inserted into the restriction sites Asu II/Sal I in the downstream of GAP promoter in the vector pGAPZαA (FIG. 1) by PCR and restriction to obtain recombinant plasmids referred as pGM plasmid.

PGAP-PpMIT1-AOX1TT expression system (full length 3615 bp) was amplified from pGM plasmid by PCR with M1-GAP5 and M1-AOX1TT as the primers (Table 1), and such expression system was inserted at the Sac I/Spe I site in pAG32 (FIG. 2) as the vector. The resulted recombinant plasmid was pGMhph.

TABLE 1

Primers list

| Primer | SEQ ID NO: | Sequence |
|---|---|---|
| M1-GAP5 | 4 | 5'-CGAGCTCAGATCTTTTTTGTAGAAATGTC-3' |
| M1-AOX1TT | 5 | 5'- GACTAGTGCACAAACGAAGGTCTC-3' |
| HXS1-C-5 | 6 | 5- CCGGAATTCTAGTCACGGATTGCTTC -3 |
| HXS1-C-3 | 7 | 5- ACATGCATGCGTTCCCAATAGATTTCACAA -3 |

2. Electroporation of *Pichia* and Selection of GS115-MIT1 Strain

The PpMIT1 overexpression plasmid (pGMhph) was electroporated into *Pichia* strain GS115 and coated on 4 YPD solid medium added with hygromycin, cultured in incubator at 30° C. for 48 to 72 hours. The monoclone on the plates were picked into a 10 ml YPD+hygromycin liquid medium, the genome was extracted and detected by PCR after being cultured in shaker at 30° C. The correct *Pichia* strain identified by PCR detection and sequencing was named as GS115-MIT1.

3. Aox Color Reaction

Each strain was cultured in YNB liquid medium containing 0.5% (v/v) methanol, 1% glycerol, 1% glycerol+0.5% (v/v) methanol respectively as carbon source. 1 ml sample was taken during the logarithmic phase and Aox1 enzyme developing liquid was added to the centrifuged thallus to develop (see in Stasyk O. V., T. Y. Nazarko, and A. A. Sibirny. 2008. Methods of Plate Pexophagy Monitoring and Positive Selection for ATG Gene Cloning in Yeasts. *Methods in enzymology.* 451:229-239. The developing substrate was o-dianisidine).

The results were shown in FIG. 3, it can be seen that after growing in medium with glycerol, Aox enzyme activity was only shown in strain GS115-MIT1 while no enzyme activity was shown in wild strains.

4. Determination of Aox Enzyme Activity

Each strain was pre-cultured in MGY liquid medium overnight, and then transferred to YNB liquid medium containing 0.5% (v/v) methanol, 1% glycerol, 1% glycerol+ 0.5% (v/v) methanol, 0.5% (v/v) methanol respectively as the carbon source, the total protein was extracted after culture for 10 hours, the Aox1 enzyme activity was determined after being quantified by Bradford (see methods in Verduyn, C., J. P. van Dijken, and W. A. Scheffers. 1984. Colorometric alcohol assays with alcohol oxidase. *J. Microbiol. Methods* 2:15-25. The developing substrate was 2,2'-azino-di-(3-ethylbenzthiazoline sulfonate), ABTS).

Figure 4:
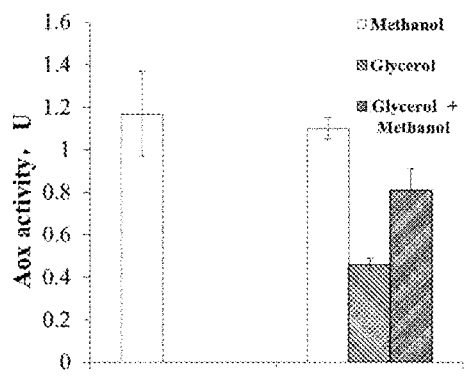
FIG. 4 shows the results of Aox enzyme activity assay of wild and GS115-MIT1 which are cultured in non-methanol or methanol containing culture medium.

It can be seen from FIG. 4 that the expression of Aox1 can be induced in strain GS115-MIT1 in medium with glycerol; all the wild strains cannot express Aox.

5. Selection of *Pichia* Strain Expressing Single Copy of GFP

GFP gene (full length 714 bp) was inserted into the restriction site SnaB I in the downstream of AOX1 promoter of vector pPIC3.5k (FIG. 9) to obtain GFP expression vector pP-GFP.

6. Selection of *Pichia* Strain Expressing Single Copy of GFP

The expression vector pP-GFP was electroporated into GS115-MIT1 strain and coated on YND plates (without histidine) and cultured in incubator at 30° C. for 48 to 72 hours. The monoclone on the plates were picked into liquid medium and the genome was extracted after being cultured in shaker at 30° C., the number of copies was verified by real-time PCR (see methods in Xuan, Y. J., X. S. Zhou, W. W. Zhang, X. Zhang, Z. W. Song, and Y. X. Zhang. 2009. An upstream activation sequence controls the expression of AOX1 gene in *Pichia pastoris*. FEMS Yeast Res. 9: 1271-1282). The *Pichia* strain expressing single copy of GFP verified by real-time PCR was named as GS115-MIT1-GFP.

Also, the expression strain Δmig1Δmig2-MIT1-GFP and Δhxs1-MIT1-GFP were constructed.

The methods of construction of expression strain Δmig1Δmig2-MIT1-GFP was as follows in detail: co-converted the expression vector pP-GFP and expression vector pGMhph into Δmig1Δmig2 strain (see in CN101857845A).

The methods of construction of expression strain Δhxs1-MIT1-GFP were as follows in detail: co-converted the expression vector pP-GFP and expression vector pGMhph into Δhxs1-MIT1 strain.

7. Measurement of the Amount of GFP Expression by Flow Cytometry

The strain GS115-MIT1-GFP was pre-cultured in YND liquid medium overnight, and then transferred to YNB liquid medium containing 0.5% (v/v) methanol, 1% glycerol, 1% glycerol+0.5% (v/v) methanol respectively as the carbon source, after sampling, the geometric mean fluorescence intensity of GFP in samples were detected by flow cytometry.

Figure 5:
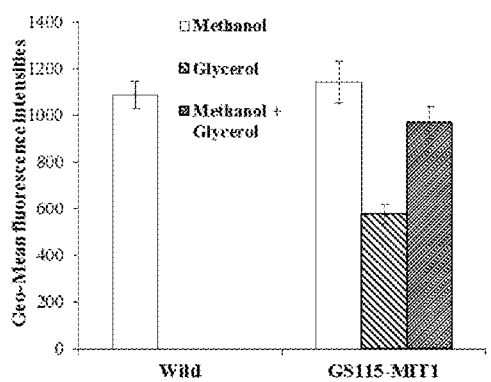
FIG. 5 shows the geometric mean fluorescence intensity of GFP of the samples by flow cytometry, and the samples are obtained from strain GS115-MIT1-GFP cultured in YND liquid culture medium overnight and then transferred to non-methanol or methanol containing culture medium.

As shown in FIG. 5, the expression of exogenous polypeptide GFP can be induced in GS115-MIT1 in the presence of glycerol.

Example 2

The Expression Driven by AOX1 Promoter can be Induced in the Presence of Glycerol or Glucose in Pichia Strain 1. Construction of the Plasmid in which the HXS1 Gene was Knocked Out The Zeocin resistance gene Sh ble fragment was cut off from plasmid pGAPZαA by BamH I and Sal I enzyme, and inserted into pUC18 plasmid (FIG. 10) digested with BamH I and Sal I enzyme, the resulted plasmid was named as pUC18-ble plasmid. GS115 genome was used as the template, firstly, the promoter region outside the 5' terminal of the PpHXS1 gene (the upstream of initiation codon ATG) was amplified with primers HS1-5F/HS1-5R, the size of amplified product was 728 bp. The 3'terminal of PpHXS1 gene (downstream of termination codon) was amplified with primers HS1-3F/HS1-3R, the size of amplified product was 1011 bp, and gel extraction of target size fragments was performed.

The recovered DNA fragment of promoter outside the 5' terminal of PpHXS1 gene was double digested with EcoRI and BamHI, and then the fragments were recovered. pUC18-ble plasmid was double digested with EcoRI and BamHI and then the fragments were recovered. The two recovered fragments were linked overnight and then transformed into E. coli, PCR was performed to select the positive clone, which was named as pUC18-(HS1 5'-ble).

The plasmid constructed by the former step was double digested with SalI and SphI, and then the fragments were recovered. The 3' terminal DNA fragment of PpHXS1 gene was also double digested with SalI and SphI. The two fragments were linked overnight and then transformed into E. coli, PCR was performed to select the positive clone, which was named as pUC18-(HS1 5'-ble-HS1 3').

TABLE 2

Primers used in PpHXS1 knockout

| Primer Name | SEQ ID NO: | Sequence |
|---|---|---|
| HS1-5F | 11 | 5'-CCGGAATTCTAGTCACGGATTGCTTC-3' |
| HS1-5R | 12 | 5'-CGCGGATCCAGTCTGAAATAGGCTCAGACAT-3' |
| HS1-3F | 13 | 5'-ACGCGTCGACATGCCTATTGAACAAGACTATT-3' |
| HS1-3R | 14 | 5'-ACATGCATGCGTTCCCAATAGATTTCACAA-3' |

2. Construction of Gene Deleted Strain Δhxs1 pUC18-(HS1 5'-ble-HS1 3') plasmid was double digested with EcoRI and SphI, and the PpHXS1 knockout fragment HS1 5'-ble-HS1 3' of 3350 bp was recovered by gel extraction.

20 μl recovered PpHXS1 knockout fragment HS1 5'-ble-HS1 3' (with a concentration more than 50 ng/μl) and 80 μl Pichia GS115 competent cells were mixed on ice, electroporation was conducted according to the methods of experiment steps. 50 μl resuscitated electroporated bacterial liquid was coated on YP+Glycerol solid medium added with Zeocin, the selection plates were inverted in an incubator at 30° C. for 2 to 3 days, when a colony can be observed by naked eye, the colony was picked into YP+Glycerol liquid medium added with Zeocin and cultured for 2 to 3 days. PCR was performed to prove positive strain in which the PpHXS1 was deleted, and said strain was named as Δhxs1.

3. Construction of Δmig1Δmig2-MIT1 and Δhxs1-MIT1

Plasmid pGMhph was electroporated into Pichia Δmig1Δmig2 and Δhxs1, and then coated on four YPD plates added with hygromycin and cultured in an incubator at 30° C. for 48 to 72 hours. The monoclone on the plate was picked into 10 ml YPD+hygromycin liquid medium, after culture on a shaker at 30° C., the genome was extracted and detected by PCR. The correct Pichia strains verified by PCR and sequencing were named as Δmig1Δmig2-MIT1 and Δhxs1-MIT1, respectively.

4. Aox Color Reaction

Δmig1Δmig2-MIT1 and Δhxs1-MIT1 were cultured in YNB liquid medium containing 1% glycerol, 1% glycerol+0.5% (v/v) methanol, 1% glucose, 1% glucose+0.5% (v/v) methanol respectively as the carbon source, 1 ml sample was taken during logarithmic phase and centrifuged, Aox1 enzyme activity developing liquid was added to the centrifuged thallus to develop.

Figure 6:
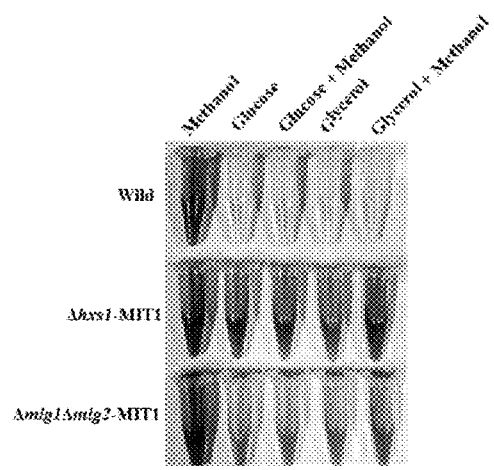
FIG. 6 shows the Aox enzyme developing of the centrifuged thallus from 1 ml culture medium which is obtained from wild and Δmig1Δmig2-MIT1 and Δhxs1-MIT1 strains in logarithmic phase cultured in non-methanol or methanol containing culture medium.

The results were shown in FIG. 6, it can be seen that in medium with glycerol or glucose, only strain Δmig1Δmig2-MIT1 and Δhxs1-MIT1 had enzyme activity.

5. Aox Enzyme Activity Assay

Each strain was cultured in YNB liquid medium containing 1% glycerol, 1% glycerol+0.5% (v/v) methanol, 1% glucose, 1% glucose+0.5% (v/v) methanol and 0.5% (v/v) methanol respectively as the carbon source, the total protein was extracted during logarithmic phase, the Aox1 enzyme activity was determined after Bradford quantity.

Figure 7:
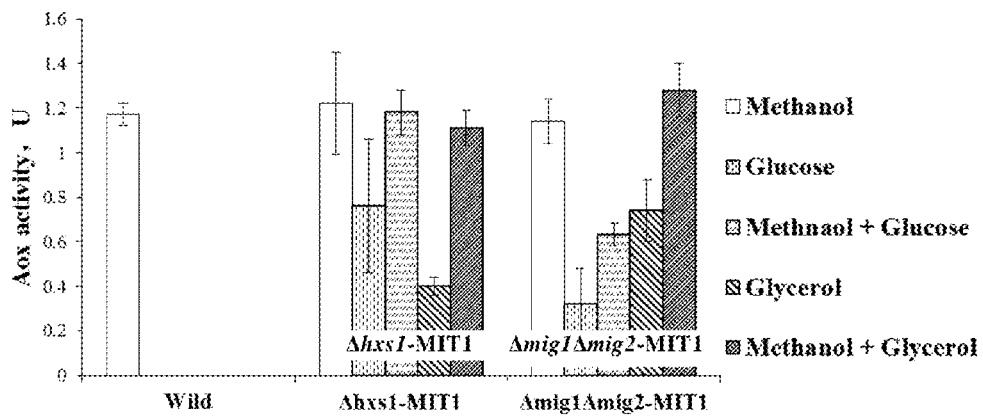
FIG. 7 shows the results of Aox enzyme activity assay of the total protein after Bradford quantity and the total protein is obtained from wild and Δmig1Δmig2-MIT1 and Δhxs1-MIT1 strains in logarithmic phase cultured in non-methanol or methanol containing culture medium.

It can be seen from FIG. 7 that the expression of Aox1 can be induced in strains Δmig1Δmig2-MIT1 and Δhxs1-MIT1 with medium containing glycerol or glucose while the expression of Aox cannot be induced in the wild strains.

6. Detection of the Amount of GFP Expression in Δmig1Δmig2-MIT1 and Δhxs1-MIT1 by Flow Cytometry Δmig1 Δmig2-MIT1-GFP and Δhxs1-MIT1-GFP were pre-cultured in liquid medium overnight and then transferred into YNB liquid medium containing 0.5% (v/v) methanol, 1% glycerol, 1% glycerol+0.5% (v/v) methanol, 1% glucose and 1% glucose+0.5% (v/v) methanol respectively as the carbon source, after sampling the geometric mean fluorescence intensity of GFP in samples was detected by flow cytometry.

As shown in FIG. 8, the expression of exogenous polypeptides GFP can be induced in Δmig1Δmig2-MIT1 and Δhxs1-MIT1 in the presence of glycerol or glucose.

Example 3

The Expression Driven by AOX1 Promoter can be Induced in the Presence of Glycerol or Glucose in Pichia Strain Δmig1Δmig2Δnrg1-MIT1

1. Construction of the Plasmid in which the NRG1 Gene was Knocked Out

With GS115 genome as the template, Primers 5'NRG1-F/5'NRG1-R were used to amplify the region outside the 5' terminal of PpNIG1 gene to obtain a fragment of 320 bp, the amplified product was named as 5'NRG1, gel extraction of 5'NRG1 fragment was performed. The above resulted 5'NRG1 fragment was double digested with Sac I and Sma I, and linked to a pUC18 plasmid also double digested with Sac I and Sma I to form pUC18(SacI-5'NRG1-SmaI). Vector pUC18(SacI-5'NRG1-SmaI) was used to transform E. coli competence cells and colony PCR was conducted to select positive clone.

Then, with plasmid pRDM054 as the template, primers HYG-F and HYG-R were used to amplify hygromycin B resistance gene HPH with the size of 1648 bp. The resulted HPH fragment was double digested with Sma I and XbaI, and linked to the vector pUC18(SacI-5'NRG1-SmaI) which was also double digested with Sma I and XbaI to from the vector pUC18(SacI-5'NRG1-SmaI-HPH-XbaI). pUC18 (SacI-5'NRG1-SmaI—HPH-XbaI) was transformed into *E. coli* and colony PCR was conducted to select positive clone.

With plasmid pUC18(SacI-5'NRG1-SmaI-HPH-XbaI) as the template, primers 5'NRG1-F/NRG1-A1 were used to amplify to obtain the fragment Overlap-A. With GS115 genome as the template, primers NRG1-B2/3'NRG1-R were used to amplify the fragment Overlap-B. Then the fragment A and B were linked by Overlap PCR to obtain 5'NRG1-HPH-3'NRG1 fragment. The fragment was linked to pMD19-T vector to obtain the knockout plasmid pMD19-T (SacI-5'NRG1-SmaI-HPH-3'NRG1-SphI).

2. Construction of Δmig1Δmig2Δnrg1 Strain

The obtained SacI-5'NRG1-SmaI-HPH-3'NRG1-SphI fragment was converted into the competence double deleted strain Δmig1Δmig2, 700 μl of pre-cooled 1 mol/L sorbitol was added immediately after electroporation, and then transferred into a EP tube with 700 μl YPD liquid medium, and resuscitated on shaker at 200 r/min at 30° C. for 1 to 2 h. Finally, the bacterial liquid was coated on YPD solid plate with Zeocin, G418 and Hygromycin antibiotic. The plates were inverted in an incubator at 30° C. for 2 to 3 days. The positive transformants were detected by PCR and the positive strain was named as Δmig1Δmig2Δnrg1.

3. Construction of MIT1 Overexpression Plasmid in Triple Deleted Strain

GAP promoter was inserted into two restriction sites of Sac I/BamH I of pPIC3.5k to obtain pPG plasmid. The sequence of PpMPP1 gene was inserted into the two restriction sites of BamH I/Not I to obtain recombinant plasmid named as pPGPP1 plasmid.

4. Construction of Δmig1Δmig2Δnrg1-MIT1

Plasmid pPGPP1 was electroporated into *Pichia* strain Δmig1Δmig2Δnrg1 and coated on four YND plates without his, cultured in an incubator at 30° C. for 48 to 72 hours. The monoclone grown on the plate was picked into 10 ml YND liquid medium, after culture on shaker at 30° C., the genome was extracted and verified by PCR. The correct *Pichia* strains verified by PCR and sequencing were named as Δmig1Δmig2Δnrg1-MIT1.

5. Selection of *Pichia* Strain Expressing GFP of Single Copy

The expression vector pP-GFP was electroporated into GS115-MIT1 strain and coated on a YND plate without histidine, cultured in an incubator at 30° C. for 48 to 72 hours. The monoclone on the plate was picked into MGY liquid medium, and green fluorescence was detected under the fluorescence microscope, the transformant with fluorescence was cultured on shaker at 30° C. and then the genome was extracted, the number of copies of GFP was verified by real-time PCR (see methods in Xuan, Y. J., X. S. Zhou, W. W. Zhang, X. Zhang, Z. W. Song, and Y. X. Zhang. 2009. An upstream activation sequence controls the expression of AOX1 gene in *Pichia pastoris*. FEMS Yeast Res. 9: 1271-1282). The *Pichia* strain expressing single copy GFP verified by real-time PCR was named as Δmig1Δmig2Δnrg1-MIT1-GFP.

6. Aox Enzyme Activity Assay

Δmig1Δmig2Δnrg1-MIT1 strain was cultured in YNB liquid medium containing 1% glycerol, 1% glycerol+0.5% (v/v) methanol, 1% glucose, 1% glucose+0.5% (v/v) methanol and 0.5% (v/v) methanol respectively as the carbon source, sampling in the logarithmic phase and the total protein was extracted, and determine the Aox1 enzyme activity after Bradford quantity.

As shown in FIG. 11, the expression of Aox1 can be induced in strain Δmig1Δmig2Δnrg1-MIT1 in medium containing glycerol or glucose while the expression of Aox cannot be induced in the wild strains.

7. Detection of the Amount of GFP Expression in Δmig1 Δmig2 Δnrg1-MIT1 by Flow Cytometry Δmig1Δmig2Δnrg1-MIT1-GFP was pre-cultured in liquid medium overnight and then transferred into YNB liquid medium with 0.5% (v/v) methanol, 1% glycerol, 1% glycerol+0.5% (v/v) methanol, 1% glucose and 1% glucose+0.5% (v/v) methanol respectively as the carbon source, after sampling the geometric mean fluorescence intensity of GFP in samples was detected by flow cytometry.

Figure 12:
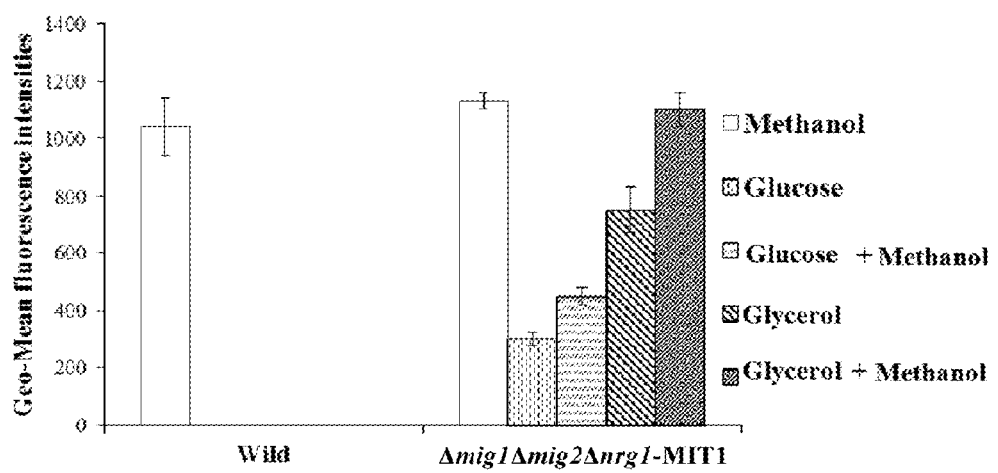
FIG. 12 shows the geometric mean fluorescence intensity of GFP of the samples by flow cytometry, and the samples are obtained from wild and Δmig1Δmig2Δnrg1-MIT1 strains cultured in non-methanol or methanol containing culture medium.

As shown in FIG. 12, the expression of exogenous polypeptides GFP can be induced in Δmig1 Δmig2Δnrg1-MIT1 in the presence of glycerol or glucose.

TABLE 3

| Primers used in PpNIG1 knockout | | |
|---|---|---|
| Primer name | SEQ ID NO: | Sequence |
| 5'NRG1-F | 15 | 5'- CGAGCTCCTGTGCCTATTACCCCCCTT -3' |
| 5'NRG1-R | 16 | 5'- TCCCCCGGGAACAGATAACCAAAACGGACG -3' |
| 3'NRG1-F | 17 | 5- GCTCTAGAGTATTTATTTACGGATTGGA -3' |
| 3'NRG1-R | 18 | 5'- ACATGCATGCCACCACTTTTTGAATCTCGG -3' |
| HYG-F | 19 | 5'- TCCCCCGGGAGCTTGCCTTGTCCCCGCCG -3' |
| HYG-R | 20 | 5'- GCTCTAGATCGACACTGGATGGCGGCGT -3' |
| NRG1-A1 | 21 | 5'-TCCAATCCGTAAATAAATACTCGACACTGGATGGCGGCGT-3' |
| NRG1-B2 | 22 | 5'-ACGCCGCCATCCAGTGTCGAGTATTTATTTACGGATTGGA-3' |

All references cited in the present invention are incorporated herein by reference as each one of them was individually cited. Further, it should be understood that various modifications and/or changes are obvious to a skilled person in the art, in view of above teaching of the subject invention, which all fall within the scope defined by the appended claims.

The invention claimed is:

1. A method for eliminating the dependence on methanol as the single carbon source of a methanol inducible promoter for driving the expression of an exogenous polypeptide encoding gene, comprising:
   (1) providing a methylotrophic yeast, said methylotrophic yeast comprises:
   expression cassette 1, which expresses an exogenous Mit1 polypeptide; and
   expression cassette 2, which comprises a methanol inducible promoter and an exogenous polypeptide encoding gene which is operably linked to the promoter;
   (2) culturing the methylotrophic yeast in (1) under the conditions wherein there is no methanol or methanol is not the only carbon source,
   wherein the condition of when methanol is not the only carbon source is a condition wherein the carbon source comprises glycerol and methanol or a condition containing glucose and methanol;
   wherein the Mit1 polypeptide is
   a polypeptide with an amino acid sequence as set forth in SEQ ID NO: 2 or a polypeptide with an amino acid sequence having more than 95% identity to the amino acid sequence as set forth in SEQ ID NO: 2 and having the ability to induce a methanol inducible promoter to express an exogenous polypeptide with carbon sources other than methanol.

2. The method according to claim 1, wherein said methanol inducible promoter comprises: AOX1 promoter, DHAS promoter, DAS promoter, FDH promoter, FMDH promoter, MOX promoter, AOX2 promoter, ZZA1, PEX5-, PEX8-, PEX14-promoter, PMP20 promoter, PMP47 promoter, AOD1 promoter, or AOD2 promoter.

3. The method according to claim 1, wherein the methylotrophic yeast comprises: *Pichia, Hansenula, Candida*, or *Torulopsis*.

4. The method according to claim 3, wherein the *Pichia* comprises GS115, *Pichia* wherein the MIG1 gene and MIG2 gene are unexpressed, *Pichia* wherein the NRG1 gene, MIG1 gene and MIG2 gene are unexpressed, or *Pichia* wherein the HXS1 gene is unexpressed.

5. The method according to claim 1, wherein the expression cassette 1 comprises a promoter and a Mit1 polypeptide encoding gene which is operably linked to the promoter.

6. The method according to claim 5, wherein the promoter comprises a constitutive promoter, an inducible promoter, a tissue or organ specific promoter, or a temporal and spatial specificity expression promoter.

7. The method according to claim 1, wherein a yeast medium containing glycerol and/or glucose is used in step (2).

8. A recombinant methylotrophic yeast, said methylotrophic yeast comprises:

expression cassette 1, which expresses an exogenous Mit1 polypeptide, the Mit1 polypeptide being a polypeptide with an amino acid sequence as set forth in SEQ ID NO: 2 or a polypeptide with an amino acid sequence having more than 95% identity to the amino acid sequence as set forth in SEQ ID NO: 2 and having the ability to induce a methanol inducible promoter to express an exogenous polypeptide with carbon sources other than methanol; and expression cassette 2, which comprises a methanol inducible promoter and an exogenous polypeptide encoding gene which is operably linked to the promoter.

9. The recombinant methylotrophic yeast according to claim 8, wherein the methylotrophic yeast comprises: *Pichia, Hansenula, Candida,* or *Torulopsis*.

10. The recombinant methylotrophic yeast according to claim 9, wherein the *Pichia* comprises GS115, *Pichia* wherein the MIG1 gene and MIG2 gene are unexpressed, *Pichia* wherein the NRG1 gene, MIG1 gene and MIG2 gene are unexpressed, or *Pichia* wherein the HXS1 gene is unexpressed.

11. The recombinant methylotrophic yeast according to claim 10, wherein the MIG1 gene has a nucleotide sequence as set forth in SEQ ID NO: 9;

the MIG2 gene with a nucleotide sequence as set forth in SEQ ID NO: 10;

the HXS1 gene with a nucleotide sequence as set forth in SEQ ID NO: 3; or the NRG1 gene with a nucleotide sequence as set forth in SEQ ID NO:8.

* * * * *